United States Patent
Gombert et al.

(10) Patent No.: US 10,004,563 B2
(45) Date of Patent: Jun. 26, 2018

(54) HOLDING DEVICE HAVING AT LEAST ONE CLAMPING JAW FOR A ROBOTIC SURGICAL SYSTEM

(71) Applicant: gomtec GmbH, Seefeld (DE)

(72) Inventors: Bernd Gombert, Worthsee (DE); Leopold Krausen, Munich (DE); Patrick Rothfuss, Hallbergmoos (DE)

(73) Assignee: GOMTEC GMBH, Seefeld (DE)

( * ) Notice: Subject to any disclaimer, the term of this patent is extended or adjusted under 35 U.S.C. 154(b) by 384 days.

(21) Appl. No.: 14/768,755

(22) PCT Filed: Feb. 4, 2014

(86) PCT No.: PCT/EP2014/052100
§ 371 (c)(1),
(2) Date: Aug. 18, 2015

(87) PCT Pub. No.: WO2014/127984
PCT Pub. Date: Aug. 28, 2014

(65) Prior Publication Data
US 2015/0374445 A1    Dec. 31, 2015

(30) Foreign Application Priority Data
Feb. 19, 2013  (DE) .................. 10 2013 002 813

(51) Int. Cl.
*A61B 17/00*      (2006.01)
*A61B 19/00*      (2006.01)
(Continued)

(52) U.S. Cl.
CPC .......... *A61B 19/2203* (2013.01); *A61B 34/30* (2016.02); *A61B 46/10* (2016.02);
(Continued)

(58) Field of Classification Search
CPC ......... A61B 90/57; A61B 17/28; A61B 17/29; A61B 2017/2926; A61B 2017/2947;
(Continued)

(56) References Cited

U.S. PATENT DOCUMENTS

| 5,954,446 A | 9/1999 | Ireland |
| 2009/0247819 A1 | 10/2009 | Wilson |
| 2012/0303025 A1* | 11/2012 | Garrison ................ A61B 17/29 606/51 |

FOREIGN PATENT DOCUMENTS

| DE | 19625729 A1 | 1/1998 |
| EP | 1931275 B1 | 3/2011 |
| EP | 2335635 A1 | 6/2011 |

* cited by examiner

*Primary Examiner* — Jonathan Miles
*Assistant Examiner* — Wade Miles
(74) *Attorney, Agent, or Firm* — Schwabe Williamson & Wyatt, PC

(57) ABSTRACT

The invention relates to a holding device (1) for a robotic surgical system, said holding device having a clamping device (11') for removably holding a surgical object (12), said clamping device comprising at least two clamping jaws (14, 15) and a bearing part (8) on which at least one of the clamping jaws (10, 15) is movably mounted, and having at least one actuation element (18, 19) for actuating at least one of the clamping jaws (14, 15). The holding device (11) can be provided with a sterile encasement (13) in an intended use. According to the invention, the actuation element (18, 19) is guided in an axially movable manner on the bearing part (8).

13 Claims, 5 Drawing Sheets

(51) Int. Cl.
*B25J 15/02* (2006.01)
*B25J 19/00* (2006.01)
*A61B 90/57* (2016.01)
*A61B 34/30* (2016.01)
*A61B 50/30* (2016.01)
*A61B 46/10* (2016.01)
*A61B 17/29* (2006.01)
*A61B 17/34* (2006.01)
*A61B 90/00* (2016.01)

(52) U.S. Cl.
CPC .............. *A61B 50/30* (2016.02); *A61B 90/57* (2016.02); *B25J 15/0206* (2013.01); *B25J 19/0075* (2013.01); *A61B 17/3421* (2013.01); *A61B 2017/2947* (2013.01); *A61B 2034/305* (2016.02); *A61B 2090/037* (2016.02)

(58) Field of Classification Search
CPC ............ A61B 2017/2939; A61B 34/30; A61B 2034/301; A61B 2034/302; A61B 2034/303; A61B 2034/304; A61B 2034/305; A61B 2034/306; A61B 34/32; A61B 34/35; A61B 34/37; A61B 5/6838; A61B 5/6884; A61B 18/1442; A61B 18/1445; A61B 18/1447; A61B 2018/1462; A61B 90/50; A61B 2018/145
See application file for complete search history.

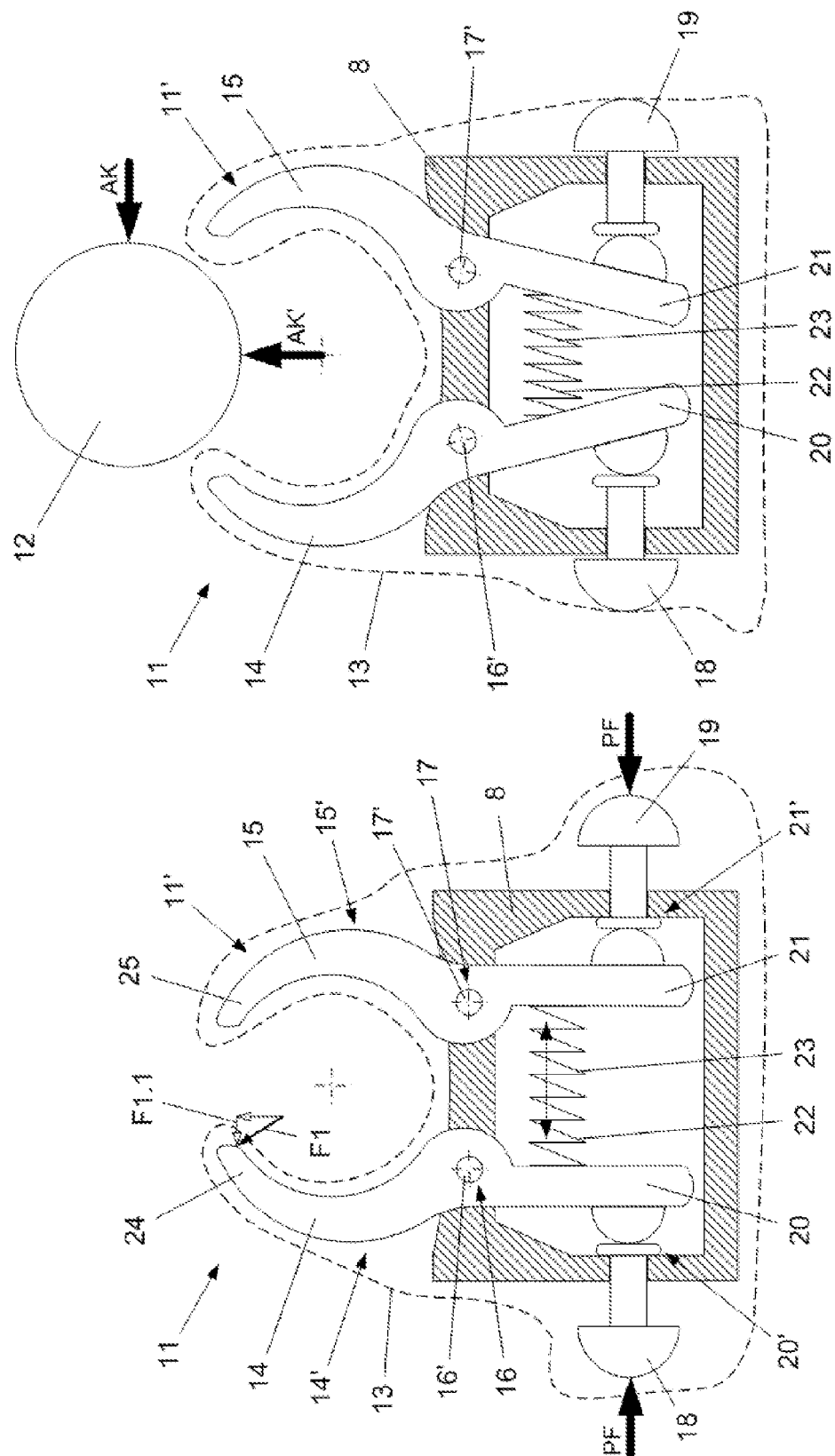

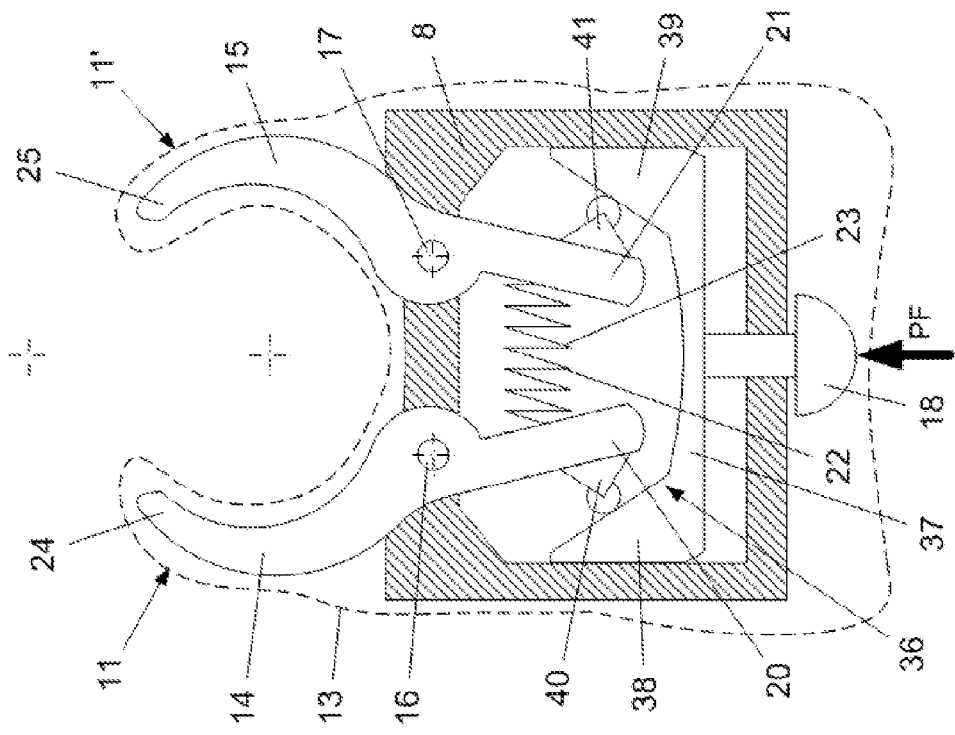
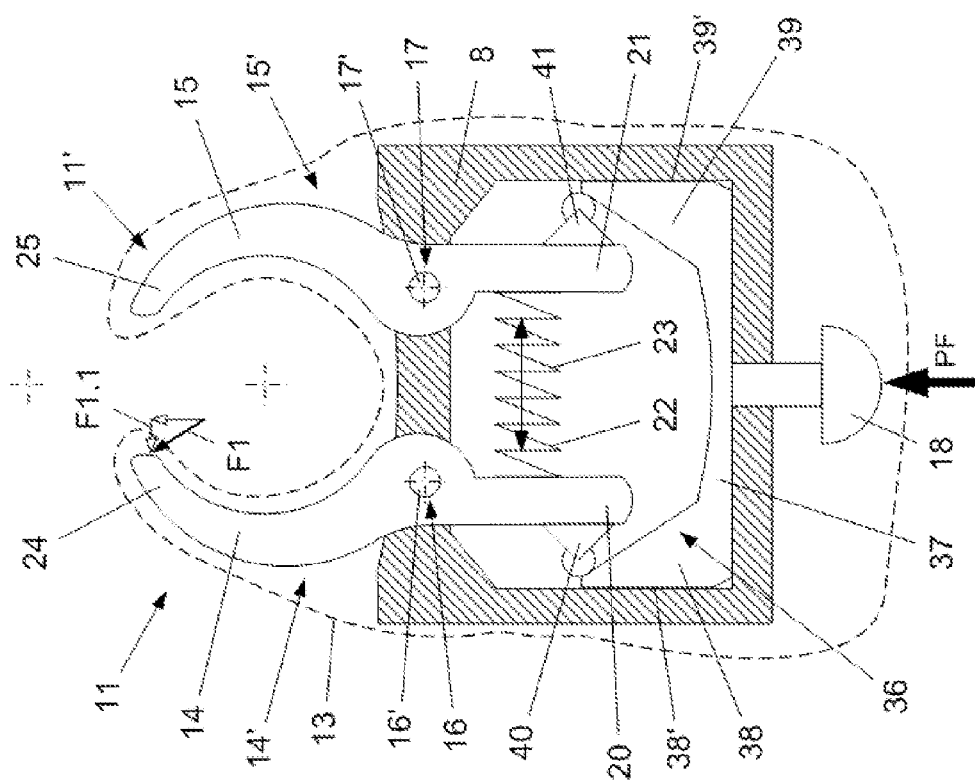

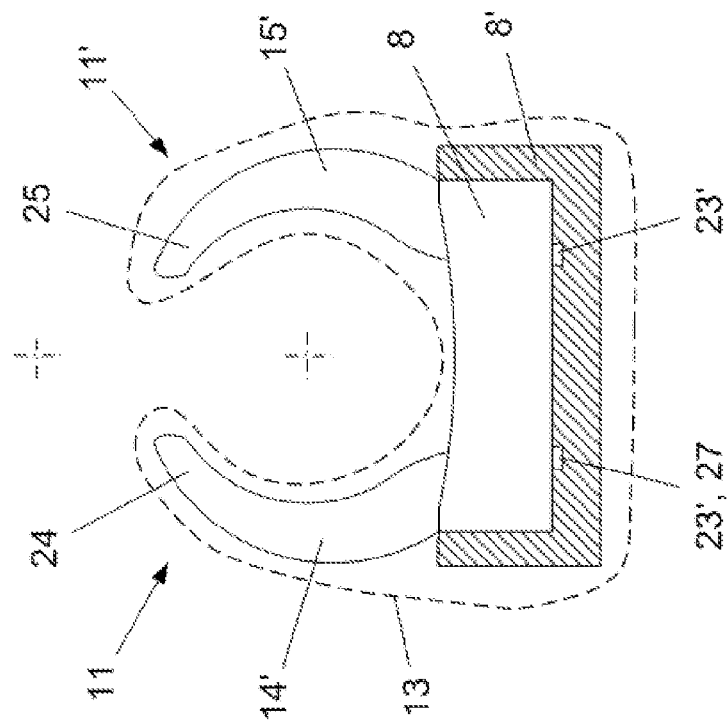
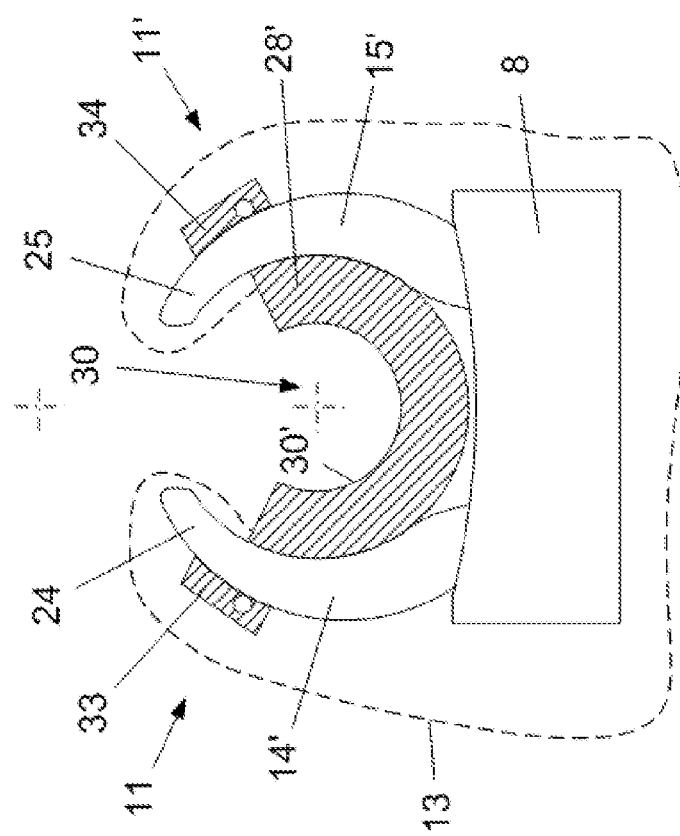

HOLDING DEVICE HAVING AT LEAST ONE CLAMPING JAW FOR A ROBOTIC SURGICAL SYSTEM

The present application is a U.S. National Phase of PCT/EP2014/052100, filed Feb. 4, 2014 entitled "HOLDING DEVICE HAVING AT LEAST ONE CLAMPING JAW FOR A ROBOTIC SURGICAL SYSTEM," which claims priority to German patent application No. 10 2013 002 813.2 filed on Feb. 19, 2013, which are incorporated herein by reference in their entirety.

The invention relates to a holding device having at least one clamping jaw, specifically for a robotic surgical system according to the preamble of claim 1.

A prototypical holding device is known from EP 1 931 275 B1. The holding device comprises a clamping device for removably holding a surgical object, comprising two clamping jaws and a bearing component. At least one of the clamping jaws is movably mounted on the bearing component, so that the clamping device can be opened for receiving the surgical object. For the actuation of the at least one movably mounted clamping jaw, an actuation element in the form of a pivotably mounted lever is attached to the holding device. For a proper use of the holding device, for example, in an operating room, the holding device is provided with a sterile cover. The pivotable lever is surrounded by the sterile cover such that the cover is moved along the path of the lever upon actuation of the lever. This can lead to tearing or damage of the protective cover upon actuation of the lever. It is furthermore not evident from the disclosure how a high force (overload) affects the surgical object as well as the clamping jaws.

DISCLOSURE OF THE INVENTION

It is therefore an object of the invention to provide a holding device which can be manually actuated without thereby damaging a protective cover thereover. In addition, the holding device should enable an automatic release of the surgical object in case of overload without damage to the clamping device or the object itself.

This object is achieved by means of a holding device for a robotic surgical system having the features specified in claim 1. Further embodiments follow from the dependent claims.

According to the invention is proposed a holding device for a robotic surgical system having a clamping device for removably holding a surgical object, said clamping device comprising at least two clamping jaws and a bearing component on which at least one of the clamping jaws is movably mounted, and having at least one actuation element for actuating at least one of the clamping jaws, wherein the holding device can be provided with a sterile cover. The actuation element according to the invention is preferably mounted in an axially movable manner on the bearing component. This has the advantage that the protective sheath is only slightly strained upon actuation of the holding device. In addition, the holding device is equipped with a first overload protection apparatus, which allows an automatic opening of the clamping device when an external force acting on the clamping device in the region of the clamping jaws reaches or exceeds a threshold value. An object held by the holding device can thus automatically—without thereby requiring use of the actuation element—be released from the clamping device. Alternatively or additionally, a second overload protection apparatus can be provided, which allows an automatic release of the holding device from an object, such as a robotic system, on which it is mounted, when an external force acting upon the clamping device reaches or exceeds a threshold value. In this case, the entire holding device is essentially torn away from the object if the external force is too large.

The actuation element is preferably mounted such that it performs a purely translatory movement along a straight line when it is actuated.

The axial movement of the actuation element is preferably transformed into a pivoting movement of the at least one clamping jaw.

The axial direction of movement of the actuation element is preferably oriented approximately perpendicular to the surface of the sterile cover in the region of the actuation element. Thus, the sterile cover is not damaged under tension and is neither torn nor pinched.

The actuation element is preferably oriented such that actuation applies a purely compressive force which—with respect to the cover—is oriented in the direction of the bearing component.

According to a preferred embodiment of the invention, the clamping device has at least one arm movably mounted on the bearing component, with at least two functional sections, of which a first functional section forms a clamping jaw and a second functional section forms an actuation extension which interacts with the actuation element.

Preferably, the arm is mounted more or less centrally on the bearing component so that the two functional sections have approximately the same length. In order to set a desired transmission relationship, the functional sections of the arm may also have a different length. Accordingly, the arm may be eccentrically movably mounted on the bearing component.

Preferably, the movably mounted arm is made in one piece.

According to a preferred embodiment of the invention, the at least one clamping jaw is biased with a spring element in the direction of closing. When the clamping device is open, the surgical object to be held can thus be placed between the clamping jaws and then held by the spring-biased clamping jaw.

The spring element is preferably formed as a helical spring, in particular a compression spring.

The first overload protection apparatus preferably comprises at least one spring element acting on the clamping jaw(s).

The threshold value of the first overload protection apparatus can, for instance, be varied by different spring elements with different spring constants. Optionally, a means for setting the threshold value, for example a set screw, may be provided.

According to a particularly preferred embodiment of the invention, a single spring element for biasing the movably mounted clamping jaw(s) is provided in the closing direction and as a first overload protection apparatus.

According to a preferred embodiment of the invention, the actuation element is coupled to at least one of the clamping jaws via a bearing, such as a sleeve bearing. In the case of a sleeve bearing, a section of the actuation element slides on a corresponding element of the clamping device when the holding device is actuated. Alternatively, the bearing can be designed as a roller or rolling bearing.

According to a further embodiment of the invention, the actuation element is coupled to a wedge mechanism for transforming the translational movement of the actuation element into a pivoting movement of at least one of the clamping jaws.

Preferably, the wedge mechanism has at least one wedge surface, along which a corresponding element, such as a section of a lever arm, moves during operation of the actuation element.

A specific embodiment of the invention is characterized in that the clamping device comprises two movably mounted clamping jaws and a single actuation element for simultaneously opening and/or closing both clamping jaws. Thus a one-handed operation of the clamping device is possible in a simple manner, so that a user can, for example, bring with his other hand the surgical object to be held into engagement with the clamping jaws.

The holding device according to the invention may, however, also have two movably mounted clamping jaws, wherein a separate actuation element is provided for each clamping jaw. Both clamping jaws can thereby be operated independently of one another.

In the latter embodiment, the two actuation elements are preferably arranged opposite one another on the bearing component. The actuation directions of the two actuation elements are preferably oriented in contrary directions, so that the operator can actuate both actuation elements, for example, by closing the thumb and forefinger. This means that the actuation elements are advantageously compressibly arranged.

Between the clamping jaws may additionally be provided an adapter element, with which the receiving cross-section between the two clamping jaws can be adapted to the surgical object to be received with respect to its cross-sectional area and/or cross-sectional shape.

Different adapter elements are preferably provided for different surgical objects.

An adapter element may be flexibly, especially bendably, designed, so that it can be arranged between the clamping jaws. An adapter element is preferably made of plastic.

According to a preferred embodiment of the invention, the adapter element is part of a cover for the holding device. The adapter element and the protective sheath thus form an integral component. The adapter element can, for example, be welded or glued to the cover. A production from the same material is also coneivable, for example through varying thicknesses of the material sections for the cover and the adapter element.

The sterile cover may preferably consist of a sheet or drape.

According to a specific embodiment of the invention it is provided that the clamping device and/or the adapter element have at least one sensor which detects the presence and/or proper seat of the surgical object and/or the adapter element between the clamping jaws and/or a characteristic of the object and/or the adapter element.

With such a sensor, it can, for example, be determined whether the overload protection apparatus has been triggered, or whether the object or the adapter element is still between the clamping jaws. Optionally, it could also be detected which adapter element or which object is disposed between the clamping jaws. In order to detect the presence of an object and/or adapter a force or proximity sensor or an optical sensor can, for example, be used. The type of held object and/or the adapter can be detected, for example, by means of known RFID technology.

According to one embodiment of the invention, a sensor may also be provided by which a force acting on the clamping device or the adapter element can be detected. The threshold value of the overload protection apparatus can be set, for instance, depending on the detected force.

The surgical object may be a sheath, a trocar sleeve, a port or any other object which is required for a surgical intervention. Here are also included, for example, endoscopes or other optical or imaging instruments.

The features disclosed in this application can be regarded individually or in any desired combination with another described feature. This also applies to features which are only rendered in combination with another described and/or illustrated feature.

BRIEF DESCRIPTION OF THE DRAWINGS

The invention will be described hereafter in greater detail on the basis of exemplary embodiments with reference to drawings.

FIG. 2 shows a holding device with a closed clamping device according to a first exemplary embodiment, FIG. 3 shows the holding device according to FIG. 2 with open clamping device, FIG. 4 shows a holding device with a closed clamping device according to a second exemplary embodiment, FIG. 5 shows the holding device according to FIG. 4 with open clamping device, FIG. 8 shows a holding device with an adapter element according to a second exemplary embodiment, and FIG. 9 shows a holding device with an overload protection apparatus.

EMBODIMENTS OF THE INVENTION

Figure 1:
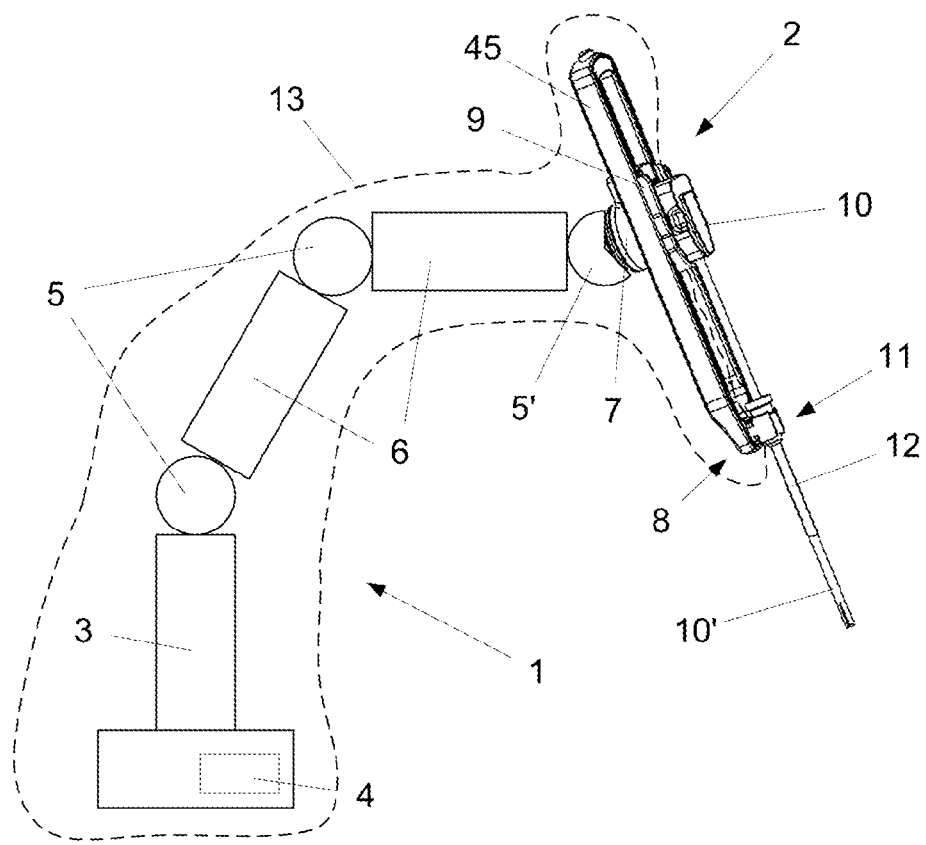
FIG. 1 shows a robotic surgical system with a holding device.

FIG. 1 shows a schematically represented robotic system with a robot 1 and a surgical device 2 fixed thereon. The robot 1 includes a base element 3, a robotic controller 4, a robotic arm with a plurality of joints 5 and a plurality of arm elements 6, as well as a robotic head 5' as the last joint. The robotic head 5' has a coupling element, to which the surgical device 2 is connected via a complementarily-formed coupling apparatus 7.

The surgical device 2 comprises an elongated, adjustable arm 45, on which is provided an interface 9 for fixing a surgical instrument 10 as well as a holding device 11 for holding a surgical object 12, such as a trocar sleeve or sheath. The holding device 11 is located here at the distal end of the arm 45. The holding device 11 is fixedly connected to the adjustable arm 45 and can preferably be formed as a structural unit with the adjustable arm 45.

At the distal end of the surgical instrument 10 is present an end effector 10', such as a scissor, a gripper, a scalpel, etc., which has been inserted through the surgical object 12.

The robot 1, the surgical device 2 and the holding device 11 are surrounded by a sterile cover 13, wherein parts of the instrument 10 and the surgical object 12 lie outside the sterile cover 13.

FIG. 2 shows an exemplary embodiment of a holding device 11 in detail. Here, the holding device 11 comprises a bearing component 8, which may be sectionally formed as a hollow body or box-shape. On the bearing component 8 is arranged a clamping device 11', which is designed for holding the object 12.

The clamping device 11' comprises two clamping arms 14', 15', which are each movably mounted on a bearing 16, 17 on the bearing component 8. In the exemplary embodiment, the clamping arms 14', 15' are pivotably mounted on the bearing component 8 and have a bearing eye 16', 17' with which a respective bearing pin engages. Each clamping arm 14', 15' has two functional sections, specifically a clamping jaw 14, 15 and an actuation extension 20, 21 which interacts with a respective axially movable actuation element 18, 19. The actuation extensions 20, 21 project into the hollow body and, in the closed position of the clamping jaws 14, 15 shown in FIG. 2, extend more or less parallel and at a distance to one another. The two bearings 16, 17 are arranged at a distance from one another on the bearing component 8.

The actuation elements 18, 19 respectively run through an opening which can be found in the wall of the bearing component 8 and are thus axially movably guided in the bearing component 8. Outside of the bearing component 8, the actuation elements 18, 19 have an actuation knob. At the other end, each actuation element 18, 19 may have an actuation plate, which interacts with the associated actuation extension 20, 21 by means of a sleeve bearing 20', 21'. On each actuation extension 20, 21 may be provided a convex raised formation.

For opening the clamping device 11' or for moving the clamping jaws 14, 15 into the open position illustrated in FIG. 3, the actuation elements 18, 19 are displaced translationally axially in the direction of the arrow PF, whereby the clamping arms 14', 15' pivot about their bearings 16, 17 and the clamping jaws 14, 15 are moved away from one another. The axial direction of movement of the actuation elements 18, 19 is preferably oriented approximately perpendicular to the surface of the sterile cover 13 in the region of these same actuation elements. The cover 13 is thus merely deflected in the direction of movement PF.

In the illustrated exemplary embodiment, the actuation elements 18, 19 are mounted on opposite-facing walls of the bearing component 8. The actuation forces in the direction of arrow PF are thus oriented in contrary directions and act as pressure forces.

Between the actuation extensions 20, 21 a spring element 22 is arranged, which is implemented as a compression spring. In the closed position of the clamping jaws 14, 15 shown in FIG. 2, the spring element 22 is biased, so that the actuation extensions 20, 21 are pressed apart. The movably mounted clamping jaws 14, 15 are thus loaded by the spring element 22 in the closing direction. If the actuation elements 18, 19 are now actuated manually in the direction of the arrows PF, the actuation extensions 20, 21 of the clamping arms 14', 15' pivot inward and the spring element 22 is pressed together, as a comparison of FIGS. 2 and 3 shows. When the compressive force is again released, the spring element 22 presses the actuation extensions 20, 21 apart. The clamping jaws 14, 15 thereby move towards each other, so that the object 12 is held at least partially enclosed by clamping.

If the object 12 is to be removed again from the clamping device 11', the clamping device 11' may again be manually actuated. Alternatively, however, the object 12 could also be pulled out of the clamping device 11' by force, whereby the clamping device 11' automatically opens and releases the object 12. For this purpose, the holding device 11 comprises an overload protection apparatus 23, which allows an automatic opening of the clamping device 11' if a manual force AK, AK' acts on the object 12 held between the clamping jaws 14, 15. When the object 12 is pulled out, a force F1 with a force component F1.1 is applied to the clamping jaws 14, 15, with the result that at least one of the clamping jaws 14, 15 pivots about the bearing 16, 17 in the direction of opening. If the force component F1.1 reaches or exceeds the threshold value of the overload protection apparatus 23, at least one of the clamping jaws 14, 15 is opened. In the illustrated exemplary embodiment, the overload protection apparatus 23 is formed by the spring element 22. A single spring element 22 is provided, both for closing of the movably mounted clamping jaws 14, 15 as well as the automatic opening of the clamping jaws 14, 15 for implementation of the overload protection apparatus 23. The overload protection apparatus 23 thus automatically shuts the clamping jaws again after ejection of the object 12, in order to prevent re-clamping of the object 12.

The functionality of the overload protection device 23 can be influenced through the design of the clamping tips 24, 25 of the clamping jaws 14, 15. At least one of the clamping tips 24, 25 is preferably shaped such that a movement of the object 12 in a plane of symmetry running between the clamping jaws 14, 15 (above and below in the drawing) results in a pivoting movement of at least one of the clamping jaws 14, 15.

Hereafter will be described in greater detail a second exemplary embodiment of the holding device 11 with reference to FIG. 4. Equal or equally acting parts are provided in FIGS. 4 and 5 with the same reference characters as in FIGS. 2 and 3. In this respect, reference is made to the description thereof. Unlike the exemplary embodiment of FIGS. 2 and 3, only a single actuation element 18 is provided here for the actuation of both clamping jaws 14, 15. The actuation element 18 is connected with a wedge mechanism 36, which comprises a plunger 37 arranged within the bearing component 8, which has wedge surfaces 38, 39 extending obliquely outward which interact with the actuation extensions 20, 21. The outer surfaces 38', 39' of the plunger 37 are guided within the bearing component 8. The wedge surfaces 38, 39 interact with bearing elements 40, 41, which are arranged on the actuation extensions 20, 21, facing the wedge surfaces 38, 39. The bearing elements 40, 41 can be designed as sleeve bearings or—as shown—as rolling or roller bearings.

If the single actuation element 18 is moved in the direction of the arrow PF, the plunger 37 is displaced linearly, whereby the bearing elements 40, 41 slide along the wedge surfaces 38, 39, and by means of the oblique orientation of the wedge surfaces 38, 39, the actuation extensions 20, 21 move inward against the force of the spring element 22. The clamping device 11' thereby opens as shown in FIG. 5. The axial direction of movement of the actuation element 18 is preferably oriented approximately perpendicular to the surface of the sterile cover 13 in the region of this same actuation element.

By varying the angle which the wedge surfaces 38, 39 take with respect to the outer surfaces 38', 39', a transmission ratio for the actuation of the clamping jaws 14, 15 is set. The steeper the wedge surfaces 38, 39 are designed, the greater the distance to be covered by the linearly guided plunger 37 in order to move the clamping jaws 14, 15 into the open position; this decreases the actuation force to be applied to the actuation element 18. The same applies in the reverse, the flatter the wedge surfaces 38, 39 extend.

The axial or translational movement of the actuation element 18 is transformed by the wedge mechanism 36 into a pivoting movement of the clamping jaws 14, 15. In the exemplary embodiment according to FIGS. 2 and 3, the conversion of the axial or translational movement of the actuation elements 18, 19 into the pivoting movement takes place through the laterally outward arrangement of the actuation elements 18, 19. In both embodiments, two movably mounted clamping jaws 14, 15 are provided, wherein it becomes clear that it may be sufficient for the opening/closing of the clamping device 11', to movably mount only one jaw 14 or 15 on the bearing component 8. The other clamping jaw 15 or 14 could be held stationary on the bearing component 8. In the exemplary embodiment according to FIGS. 2 and 3, one of the actuation elements 18, 19 could thus be dispensed with. Accordingly, the wedge mechanism 36 could be outfitted with only one wedge surface 38 or 39.

As in the first exemplary embodiment, the exemplary embodiment of the holding device 11 shown in FIGS. 4 and 5 can also be outfitted with an overload protection apparatus 23.

Figure 6:
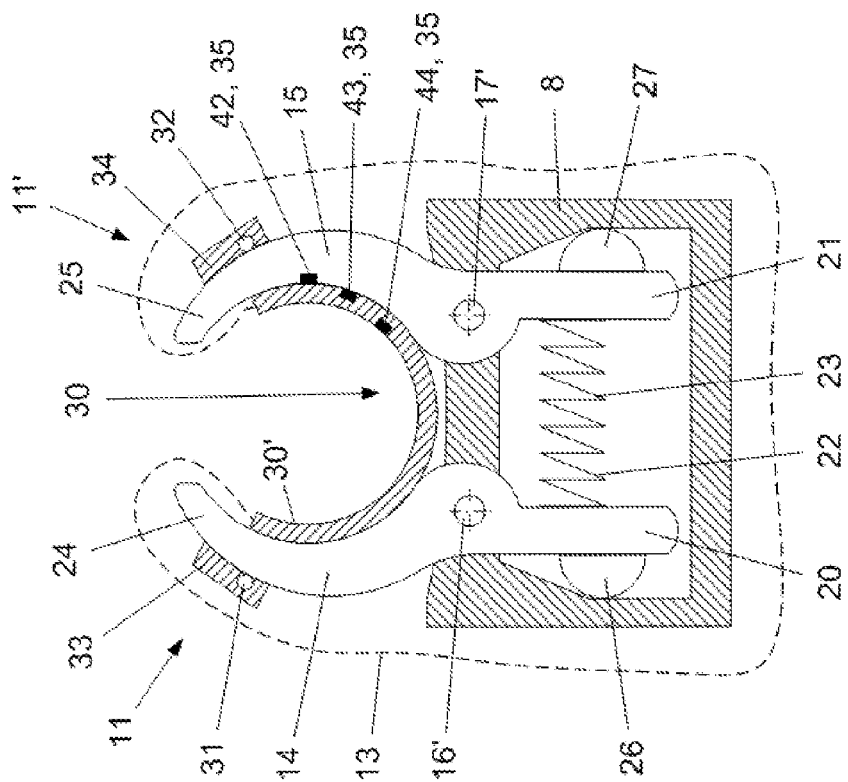
FIG. 6 shows a holding device with an open clamping device and an adapter element according to a first exemplary embodiment.
Figure 7:
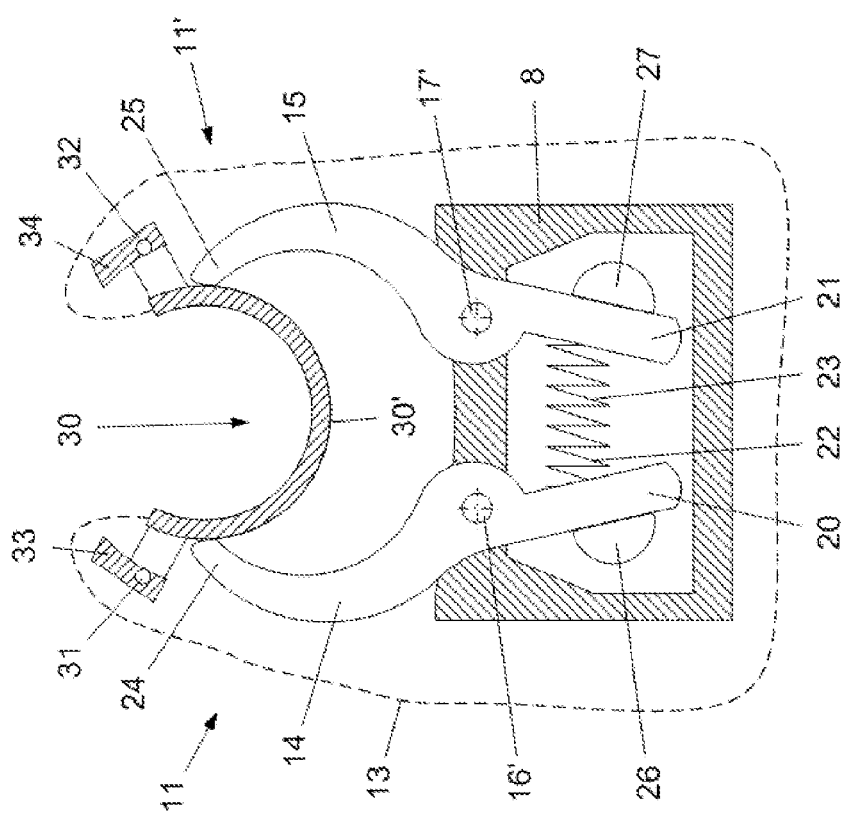
FIG. 7 shows the holding device according to FIG. 6 with closed clamping device.

FIGS. 6 and 7 show an adapter element 30, which can be disposed between the clamping jaws 14, 15 and which has an outer or peripheral contour which is fitted to the inner contour of the clamping jaws 14, 15 or to the receiving cross-section thereof. The adapter element 30 has a main body, which constitutes an open ring. Extensions with wings 33, 34 are provided on the free ends of the annular section. The extensions 33, 34 extend, starting from the annular main body, radially outward and each have an opening through which can pass the free end of a clamping jaw 14, 15 when the adapter element 30 is inserted between the clamping jaws 14, 15 as shown in FIG. 7. It should be noted that the adapter element 30 can, of course, be used on the holding device 11 of FIGS. 2 to 5. In order to reduce the friction between the adapter element 30 and clamping jaws 14, 15, rolling elements, such as balls, which roll on the clamping jaws 14, 15, can be mounted in the adapter 30. The rolling elements 31, 32 can preferably be mounted in the extensions 33, 34.

The holding device 11 or the adapter element 30 may be equipped with a sensor 35, which is connected to the robotic controller 4, for example, and which has at least one sensor 42, 43, 44. The sensor 42 is attached to at least one of the clamping jaws 14, 15, whereas the sensors 43, 44 are attached to the adapter element 30. The sensors 42, 43, 44 are thereby suitable to detect the presence and/or proper seat of the surgical object 12 and/or the adapter element 30 between the clamping jaws 14, 15 and/or a characteristic of the object 12 and/or the adapter element 30. In particular, the sensor 42 can be used to determine whether the object 12 is disposed correctly between the clamping jaws 14, 15. The sensor 43 can detect, for example, whether or not an adapter element 30 is in use, and possibly even whether the adapter element 30 has been fully released after triggering of the overload protection apparatus 23. The sensor 44 may detect whether a surgical object 12 is held by the adapter element 30. In addition, the sensor 44 could also be provided to determine the type of held object 12.

As shown in FIG. 8, the annular section of the adapter element 30 may be designed more thickly. In particular, the annular section of the adapter element 30 can be designed such that its receiving cross-section with respect to the cross-sectional area and/or the cross-sectional shape—and thus deviating from the circular shape shown here—is fitted to the surgical object 12 to be received. Thus square or oval objects 12, for instance can also be clamped. Furthermore, the adapter element 30 may be adapted to a particular shape of the object 12 and have, for example, grooves, steps or the like.

As it can additionally be seen in FIG. 8, the adapter element 30 can be connected with the sterile cover 13 or can be an integral component of the cover 13.

Instead of the above-described overload protection apparatus 23 having the spring element 22, a modified overload protection apparatus 23' may be provided, as is shown for example in FIG. 9. Here, the holding device 11 is designed with special extensions 27, which interact with an adjacent intermediary element 8' (or directly with the surgical device 2). The extensions 27 are positively received in corresponding recesses, which have an undercut. The overload protection apparatus 23' can, for example, be designed as a groove/spring connection. A detachable connection is thereby implemented, which tears away when a threshold value is reached or exceeded so that the holding device 11 is separated from the surgical device 2 and the intermediary element 8'. As shown in FIG. 9, there may be one or more such connections between the holding device 11 and the intermediary element 8'.

The invention claimed is:

1. A holding device for a robotic surgical system, said holding device having a clamping device for removably holding a surgical object, said clamping device comprising at least two clamping arms and a bearing component on which at least one of the clamping arms is movably mounted, and having at least one actuation element for actuating the at least one movable clamping arm, wherein the movable clamping arm has at least two functional sections, of which a first functional section forms a clamping arm and a second functional section forms an actuation extension which interacts with the associated actuation element, and wherein an overload protection apparatus is provided which allows an automatic opening of the clamping device when an external force acting on the clamping device reaches or exceeds a threshold value, wherein the at least one actuation element is supported in the bearing component so that it is free to move in the axial direction and extends into the interior of the bearing component, and wherein the holding device is enclosed by a sterile cover, wherein the axial direction of movement of the at least one actuation element is oriented approximately perpendicular to the surface of the sterile cover in the region of the actuation element.

2. The holding device according to claim 1, wherein the at least one movably mounted clamping arm is biased in the closing direction by a spring element.

3. The holding device according to claim 1, wherein the first overload protection apparatus comprises a spring element acting on at least one clamping arm.

4. The holding device according to claim 1, wherein a single spring element is provided both for closing the clamping device and for the first overload protection apparatus.

5. The holding device according to claim 1, wherein the actuation element is coupled with at least one of the clamping arms via a bearing.

6. The holding device according to claim 1, wherein the actuation element is coupled to a wedge mechanism, which transforms a translational movement of the actuation element into a pivoting movement of at least one of the clamping arms.

7. The holding device according to claim 1, wherein the clamping device has two movably mounted clamping arms and a single actuation element for simultaneous opening or closing of both clamping arms.

8. The holding device according to claim 1, wherein the clamping device has two movably mounted clamping arms, wherein a separate actuation element is provided for each clamping arm.

9. The holding device according to claim 8, wherein an actuation direction of a first one of the two actuation elements is opposite to an actuation direction of a second one of the two actuation elements.

10. The holding device according to claim 8, wherein the actuation elements are arranged such that they can be pressed together.

11. The holding device according to claim 1, wherein an adapter element is provided between the clamping arms.

12. The holding device according to claim 11, wherein the adapter element is a component of a cover for the holding device.

13. The holding device according to claim 1, wherein the clamping device has at least one sensor which senses the presence or the proper seating of the surgical object or an adapter element between the clamping arms or a characteristic of this object or of the adapter element.

\* \* \* \* \*